United States Patent [19]
Sinn

[11] Patent Number: 5,353,922
[45] Date of Patent: Oct. 11, 1994

[54] RETAINER FOR A COMBINED SURGICAL NEEDLE-SUTURE DEVICE POSSESSING A NEEDLE SHIELD WITH NEEDLE TIP STOP FEATURE

[75] Inventor: Hans-Jurgen F. Sinn, Fairfield, Conn.

[73] Assignee: United States Surgical Corporation, Norwalk, Conn.

[21] Appl. No.: 98,742

[22] Filed: Jul. 28, 1993

Related U.S. Application Data

[63] Continuation of Ser. No. 816,101, Jan. 2, 1992, abandoned.

[51] Int. Cl.⁵ .............................................. A61B 17/06
[52] U.S. Cl. ................... 206/63.3; 206/380; 206/468
[58] Field of Search ............... 206/63.3, 438, 380, 206/382, 468, 495, 461, 409, 480, 363, 364

[56] References Cited

U.S. PATENT DOCUMENTS

| | | |
|---|---|---|
| 3,363,751 | 1/1968 | Shave et al. . |
| 3,444,994 | 5/1969 | Kaepernik et al. . |
| 3,444,995 | 5/1969 | Sanders ........................ 206/468 |
| 3,613,879 | 10/1971 | Kemble . |
| 3,754,641 | 8/1973 | Koch ............................ 206/468 |
| 3,759,376 | 9/1973 | Lisowski . |
| 3,857,484 | 12/1974 | Thyen . |
| 3,939,969 | 2/1976 | Miller et al. . |
| 3,951,261 | 4/1976 | Mandel et al. . |
| 3,972,418 | 8/1976 | Schuler et al. . |
| 3,985,227 | 10/1976 | Thyen et al. . |
| 4,063,638 | 12/1977 | Marwood . |
| 4,089,409 | 5/1978 | Cerwin . |
| 4,089,413 | 5/1978 | Fukuyama .................... 206/382 |
| 4,120,395 | 10/1978 | Mandel et al. . |
| 4,135,623 | 1/1979 | Thyen . |
| 4,192,420 | 3/1980 | Worrell, Sr. et al. . |
| 4,249,656 | 2/1981 | Cerwin et al. . |
| 4,253,563 | 3/1981 | Komarnycky . |
| 4,284,194 | 8/1981 | Flatau . |
| 4,406,363 | 9/1983 | Aday . |
| 4,412,614 | 11/1983 | Ivanov et al. . |
| 4,413,727 | 11/1983 | Cerwin et al. . |
| 4,424,898 | 1/1984 | Thyén et al. ................. 206/63.3 |
| 4,427,109 | 1/1984 | Roshdy . |
| 4,483,437 | 11/1984 | Cerwin et al. . |
| 4,491,218 | 1/1985 | Aday . |
| 4,496,045 | 1/1985 | Ferguson et al. . |
| 4,533,041 | 8/1985 | Aday et al. . |
| 4,549,649 | 10/1985 | Roshdy ........................ 206/63.3 |
| 4,555,016 | 11/1985 | Aday et al. . |
| 4,572,363 | 2/1986 | Alpern . |
| 4,574,948 | 3/1986 | Huck et al. . |
| 4,574,957 | 3/1986 | Stead . |
| 4,615,435 | 10/1986 | Alpern et al. . |
| 4,619,364 | 10/1986 | Czopor, Jr. ................... 206/461 |
| 4,708,241 | 11/1987 | Black . |
| 4,813,537 | 3/1989 | Okuhara et al. . |
| 4,884,681 | 12/1989 | Roshdy et al. . |
| 4,887,710 | 12/1989 | Roshdy et al. . |
| 4,896,767 | 1/1990 | Pinheiro . |
| 4,903,826 | 2/1990 | Pearce ......................... 206/63.3 |
| 4,961,498 | 10/1990 | Kalinski et al. . |
| 4,967,902 | 11/1990 | Sobel et al. . |
| 5,099,994 | 3/1992 | Kalinski et al. ............. 206/63.3 |
| 5,154,283 | 10/1992 | Brown ......................... 206/63.3 |
| 5,165,540 | 11/1992 | Forney ........................ 206/364 |

FOREIGN PATENT DOCUMENTS

| | | |
|---|---|---|
| 9110452 | 10/1991 | European Pat. Off. . |
| 471458A1 | 2/1992 | European Pat. Off. . |
| 2421865 | 12/1974 | Fed. Rep. of Germany . |
| 1236064 | 6/1960 | France ........................ 206/468 |
| 673393 | 6/1966 | France . |
| WO8904685 | 6/1989 | PCT Int'l Appl. . |
| 1225798 | 3/1971 | United Kingdom ......... 206/468 |
| 1466169 | 3/1977 | United Kingdom . |

*Primary Examiner*—David T. Fidei

[57] ABSTRACT

A retainer for a combined surgical needle-suture device possesses a needle shield featuring a stop element which prevents the tip of the needle from puncturing the package in which the retainer is held.

15 Claims, 2 Drawing Sheets

RETAINER FOR A COMBINED SURGICAL NEEDLE-SUTURE DEVICE POSSESSING A NEEDLE SHIELD WITH NEEDLE TIP STOP FEATURE

This is a continuation of copending application Ser. No. 07/816,101 filed Jan. 2, 1992, now abandoned.

BACKGROUND OF THE INVENTION

This invention relates to a retainer for a combined surgical needle-suture device, also commonly referred to as an "armed suture" or simply a "suture", as part of a suture package. Retainers for sutures are known from, inter alia, U.S. Pat. Nos. 3,363,751; 3,444,944; 3,613,878; 3,759,376; 3,857,484; 3,939,969; 3,951,261; 3,972,418; 3,985,277; 4,063,638; 4,089,409; 4,120,395; 4,135,623; 4,192,420; 4,249,656; 4,253,563; 4,284,194; 4,406,363; 4,412,614; 4,413,727; 4,427,109; 4,483,437; 4,491,218; 4,496,045; 4,533,041; 4,555,016; 4,572,363; 4,574,948; 4,574,957; 4,615,435; 4,708,241; 4,813,537; 4,884,681; 4,887,710; 4,896,767; 4,961,498; and, 4,967,902.

As an essential component of a suture package, the suture retainer should possess good storing qualities, provide safety in handling and permit ready access to, and removal of, the stored sutures.

SUMMARY OF THE INVENTION

By way of meeting the foregoing criteria, there is provided in accordance with this invention a retainer for a combined surgical needle-suture device, the retainer comprising:

a) a base panel for retaining at least one surgical needle of a combined surgical needle-suture device; and, b) a needle shield mounted upon the base panel, the needle shield possessing a stop for retaining the tip of the needle.

The stop feature of the needle shield effectively prevents accidental puncture by a stored needle and permits rapid access and removal of an armed suture when desired.

DESCRIPTION OF THE PREFERRED EMBODIMENTS

Figures 1, 2:
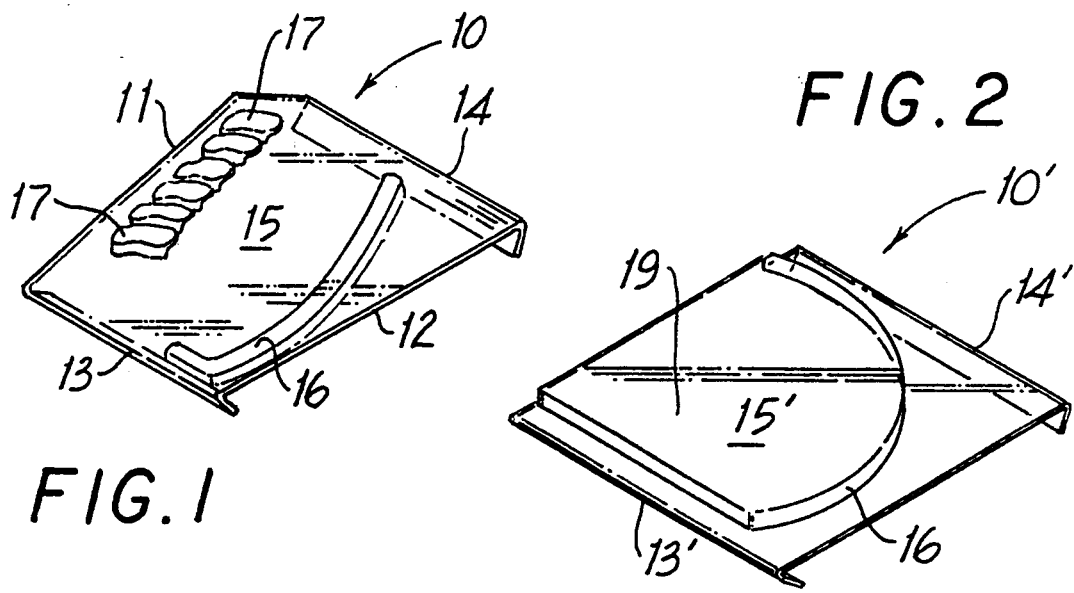
FIGS. 1 and 2 are perspective views of embodiments of a needle shield in accordance with the present invention.

As shown in FIGS. 1 and 2, needle shields 10 and 10' are each fabricated from a suitably stiff material, preferably a transparent thermoplastic resin such as polyethylene terephthalate. The needle shields are conveniently manufactured from sheets of thermoplastic resin by such known and conventional processes as thermoforming.

Figure 3:
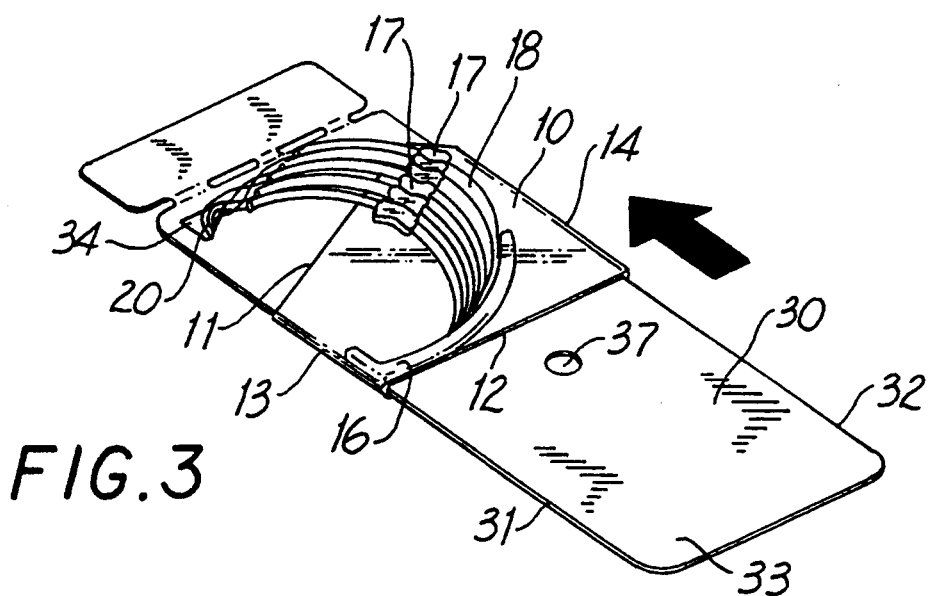
FIGS. 3 and 4 are perspective views of the obverse and reverse sides, respectively, of an armed suture retainer card with the needle shield of FIG. 1 mounted thereon.
Figure 4:
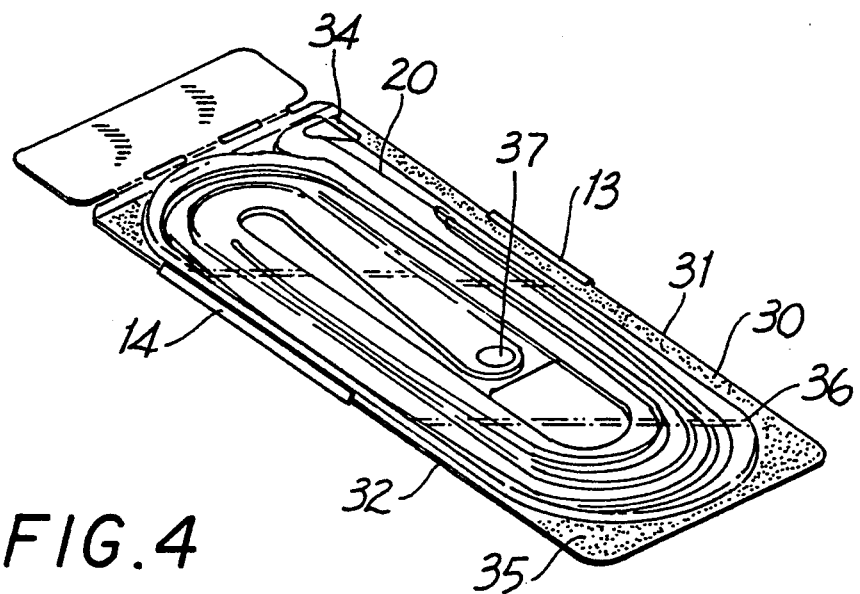

Needle shield 10 possesses top and bottom edges 11 and 12, respectively, and flanged parallel lateral edges 13 and 14, respectively, by which the needle shield grips side edges 31 and 32 of retainer base panel 30 as shown in FIGS. 3 and 4. An arcuate stop, or wall, 16 projecting upwardly from surface 15 of needle shield 10 retains the sharp tips of needle components 18 (as shown in FIG. 3) preventing the tip from causing accidental puncture of front panel 43 of peel-open suture package 40 (shown in FIGS. 5 and 6). Advantageously, stop 16 continues a short distance up lateral edge 13 to provide additional security against accidental puncture. By way of maintaining needle components 18 in a neat array upon surface 15 of needle shield 10, the surface is provided with a series of cuts defining tabs 17 which, when displaced upwardly from surface 15, provide elements for securing individual needles 18 in place. Needle securing means other than tabs 17 can, of course, be utilized, e.g., a series of approximately parallel "bumps" with a needle snap-fitted therebetween (not shown).

Needle shield 10', like needle shield 10, possesses flanged lateral edges 13' and 14' by which the needle shield grips the side edges of an armed suture retainer panel. Stop 16' is an integral element of pocket 19 and like stop 16 of needle shield 10, retains the tip of a needle thereby preventing accidental puncture of the armed suture package. However, unlike needle shield 10 in which the needles lie upon surface 15 of the shield, in needle shield 10', the stored needles are retained within pocket 19, i.e., beneath surface 15' of the shield.

Figure 5:
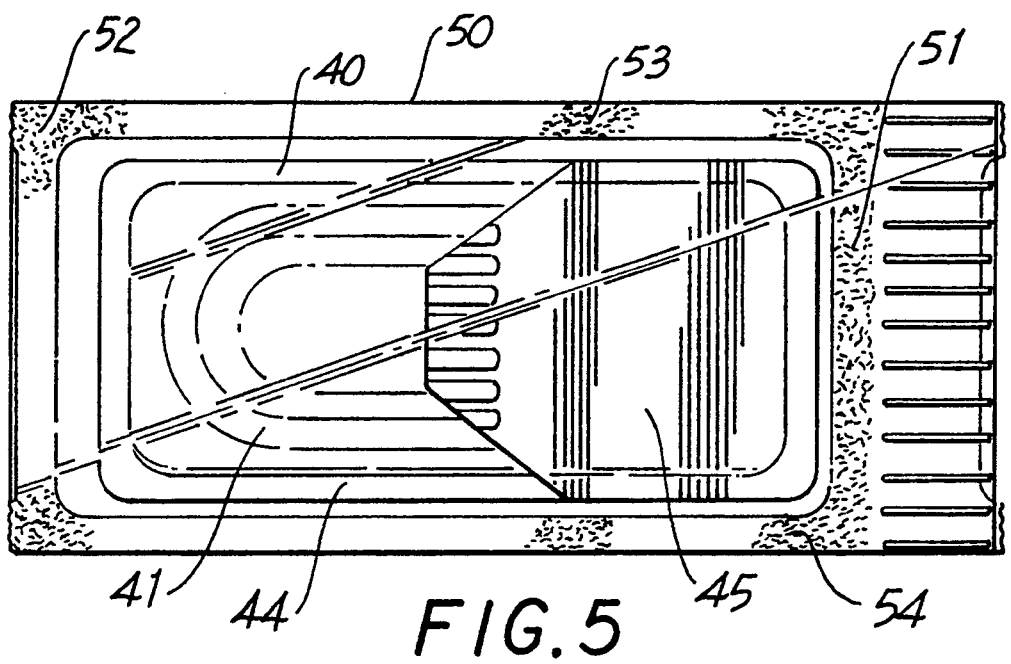
FIG. 5 is a top plan view of a suture package, including its outer breather package, suitable for packaging the armed suture retainer of FIGS. 3 and 4; and, FIG. 6 is a top plan view of the suture package of FIG. 5 removed from the breather package and opened for partial exposure of its armed suture contents.
Figure 6:
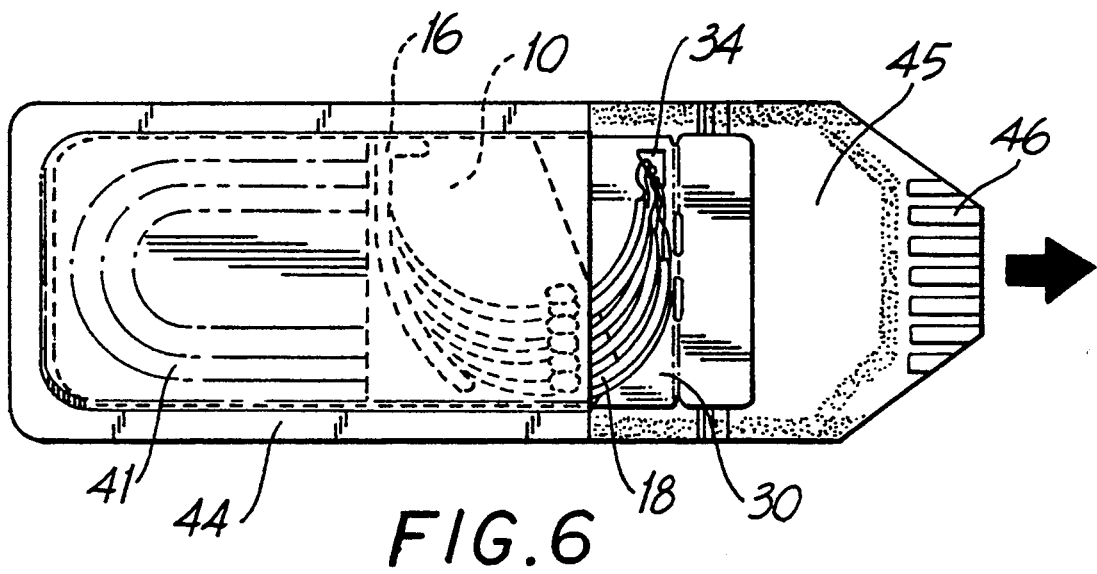

As shown in FIGS. 3 and 4 and in dotted outline in FIG. 6, the general appearance of retainer base panel 30 is that of a flat, relatively stiff panel whose longest sides 31 and 32 are parallel to each other to permit needle shield 10 or 10' to be slid onto the retainer during the packaging operation. Retainer 30 can be constructed from any of several different types of materials including various kinds of plastics, paper-foil laminate, etc. Retainer base panel 30 is more fully described, together with peel-open foil package 40 of FIGS. 5 and 6 for accommodating the loaded retainer, in pending U.S. Pat. No. 5,154,283 the contents of which are incorporated by reference herein. A similar retainer base panel which is also suitable for use herein is described in U.S. Pat. No. 5,129,511 the contents of which are incorporated by reference herein.

As shown in FIGS. 3 and 4, needle shield 10 has been mounted in place by being slid onto retainer base panel 30 in the direction indicated by the arrow. A number of armed sutures are secured in place upon retainer base panel 30, their curved needle components 18 lying flat upon a portion of obverse side 33 of the base panel and a portion of surface 15 of needle shield 10 with their suture components 20 extending through triangular shaped aperture 34 to reverse side 35 of the base panel where they occupy coiled passageway 36. The sutures can be drawn into coiled passageway 36 by applying a vacuum through orifice 37 positioned at the far end of the passageway. Under the influence of the vacuum, the sutures quickly occupy the passageway.

The fully loaded armed suture retainer of FIGS. 3 and 4 is conveniently packaged in peel-open metal foil suture package 40 of FIG. 5 shown in its outer breather package 50 following sterilization and sealing. Suture package 40 comprises an envelope 41 made up of front panel 42 joined to a rear panel (not shown) along common edges 44 employing any known and conventional adhesive. Peelable closure flap 45 completes package 40 and is advantageously provided with a knurled or embossed trapezoidally configured edge 46 to facilitate gripping. The material of construction of the front and rear panels and the closure flap is one which prevents or greatly impedes the transmission of moisture therethrough. In the embodiment shown, the walls and the closure flap are of laminate construction of a known type in which an aluminum foil is faced on its interior side with a polyolefin film such as polyethylene film. The laminate can vary in thickness from about 3 to about 5 mils and preferably from about 3.5 to about 4.5 mils.

Retainer base panel 30 is provided with an extension panel 38 which is adhesively secured to the undersurface of closure flap 45 such that when the closure flap is pulled open, it will not readily completely separate from package 40 where it might otherwise litter the operating area. To remove an armed suture from opened suture package 30, the shank of a needle is grasped by a needle gripper and pulled away from the package, usually in a direction which is more or less in the plane of the package.

Outer breather package 50 (FIG. 5) can be of known and conventional structure in which a gas-impermeable clear plastic sheet is heat sealed around its top and bottom edges 51 and 52 and its longitudinal edges 53 and 54 to a gas-permeable but sterile-secure backing sheet such as a web of spun-bonded polyolefin fiber, e.g., DuPont's Tyvek. In an improvement in this type of breather pouch which is especially suitable for use with the present invention, the fibrous backing sheet is provided with a strip of release agent, e.g., of a water-based adhesive which dries to a non-tacky finish, along its longitudinal edges which effectively eliminates the possibility of fiber-pull in the sheet when the clear plastic sheet is stripped away. Thus, as the top seal is peeled apart, the release agent along the longitudinal edges facilitates opening of the package and substantially eliminates the possibility of fiber-pull along the longitudinal edges by providing a pull-force which is substantially less than the force required to separate the fibers in the backing sheet from themselves. Also, as a result of the application of the release agent to the longitudinal edges, the pull force at the top and bottom seals required to separate the plastic layer from the fibrous backing sheet is slightly greater than the pull force required to separate the two layers at the side edges. Thus, after the initial pull separates the sheets at the top seal, it is easier to open the rest of the package by pulling the sheets apart since the force required to separate the sheets at the longitudinal edges is less than the force required to separate the initial top heat seal.

The improved breather pouch can be manufactured on an apparatus which feeds a web of fibrous backing material, e.g., Tyvek, having at least two continuous longitudinally directed strips of release agent material applied thereon at regular intervals starting at the first edge of the web and terminating at the second longitudinal edge. The apparatus feeds the web of Tyvek material and a web of plastic material, preferably polyethylene, to a position to enclose suture packages placed in rows between the plastic and Tyvek layers. This assembly is then fed to a heat seal device which simultaneously provides transverse and longitudinal heat seals to seal the suture packages between the two layers. Preferably, the plastic web is vacuum formed to provide recesses or pockets to accept the suture packages thereon. The Tyvek then overlays the plastic and suture packages and the heat seal device seals about the recesses. Alternately, the release agent material may be positioned in longitudinal strips between the tyvek and plastic layers prior to the heat sealing step, so that the heat seal is through the release agent between the two layers of material. It is preferred, however, that the release agent material be applied directly to the Tyvek layer.

A heat seal platen is applied to the webs to form the seals for adjacent packages. The assembly is then advanced to a cutter mechanism which cuts the pouches just below the transverse seal to form the bottom of one package and along the longitudinal seals, while ensuring that the top edge seals of the individual packages include the gripping tab formed for each package which facilitates separation of the plastic layer from the Tyvek layer to open the pouch.

It will be thus seen that the objects set forth above, among those made apparent from the preceding description, are efficiently attained, and since certain changes can be made in the above construction and different embodiments of the invention could be made without departing from the scope thereof, it is intended that all matter contained in the above description or shown in the accompanying drawing shall be interpreted as illustrative and not in a limiting sense.

What is claimed is:

1. A retainer for a combined surgical needle-suture device which comprises:
   a) a base panel configured to enclose at least a portion of a combined surgical needle-suture device; and
   b) a needle shield positioned on said base panel, said needle shield defining an exterior needle retaining surface including needle holding means formed in said retaining surface for retaining an intermediate portion of a surgical needle, said needle retaining surface further including an outwardly projecting needle stop positioned to engage a pointed tip of a surgical needle retained in said needle holding means.

2. The retainer of claim 1 wherein the base panel possesses parallel lateral sides and the needle shield possesses flanged parallel lateral sides for gripping contact with the parallel lateral sides of the base panel.

3. The retainer of claim 1 wherein the needle shield is formed from a synthetic resin.

4. The retainer of claim 1 wherein the needle shield is formed from a transparent synthetic resin.

5. The retainer of claim 1 wherein the needle shield is formed from polyethylene terephthalate.

6. The retainer of claim 1 wherein the needle shield possesses a pocket for receiving the pointed end of the needle.

7. The retainer of claim 6 wherein the stop is an integral part of a pocket for receiving the needle tip.

8. The retainer of claim 1 wherein the needle shield possesses needle-gripping means.

9. The retainer of claim 8 wherein the needle-gripping means comprises a needle gripping tab.

10. The retainer of claim 1 wherein base panel possesses means for enclosing the suture of the combined surgical needle-suture device.

11. The retainer of claim 10 wherein the means for enclosing the suture comprises a coiled passageway.

12. A retainer for a combined surgical needle-suture combination, the retainer comprising:
   a) a base panel having means for enclosing at least one suture of a combined needle-suture device; and
   b) a needle shield configured and dimensioned to be mounted on said base panel, said needle shield and base panel defining a cavity for enclosing at least the pointed tip of at least one needle between the needle shield and the base panel, the needle shield having a projection formed thereon, said projection defining a stop positioned to contact a pointed tip of a surgical needle and thereby retain at least a pointed tip of a needle of a combined surgical needle-suture device between said base panel and said needle shield.

13. The retainer of claim 12, wherein the base panel has parallel lateral sides and the needle shield has flanged parallel lateral sides for gripping contact with the parallel lateral sides of the base panel.

14. A retainer as in claim 12 wherein said needle shield includes a top wall and at least one side wall.

15. A retainer for a combined surgical needle-suture device which comprises:
 a) a base panel having means for retaining at least a portion of a combined surgical needle-suture device;
 b) a needle shield mounted upon the base panel, said needle shield and base panel defining a cavity for enclosing a needle of a combined surgical needle-suture device between said base panel and said needle shield; and
 c) a flexible outer package into which said base panel and said needle shield can be placed,
    said needle shield possessing a projection thereon, said projection defining a stop positioned to contact a pointed tip of a surgical needle and thereby prevent accidental puncturing of said flexible outer package.

* * * * *